US006417397B1

(12) United States Patent
Goodman et al.

(10) Patent No.: US 6,417,397 B1
(45) Date of Patent: Jul. 9, 2002

(54) N-SUBSTITUTED ALKYLAMINO ACIDS FOR USE AS AMINO-PROTECTING GROUPS (75) Inventors: Murray Goodman, La Jolla, CA (US); Christopher J. Creighton, East Norriton, PA (US)

(73) Assignee: The Regents of the University of California, San Diego, La Jolla, CA (US)

( * ) Notice: Subject to any disclaimer, the term of this patent is extended or adjusted under 35 U.S.C. 154(b) by 0 days.

(21) Appl. No.: 09/609,565

(22) Filed: Jun. 30, 2000

Related U.S. Application Data (60) Provisional application No. 60/157,435, filed on Oct. 4, 1999.

(51) Int. Cl.[7] .............................................. C07C 233/00
(52) U.S. Cl. ....................................... 564/123; 564/133
(58) Field of Search .................................. 564/133, 123

(56) References Cited

FOREIGN PATENT DOCUMENTS

| EP | 0933365 A2 | * | 8/1998 |
| EP | 0 933 365 A2 | | 8/1999 |
| WO | WO 95/26360 | * | 3/1994 |
| WO | WO 95/12581 A1 | | 5/1995 |
| WO | WO 95/26360 A1 | | 10/1995 |
| WO | WO 97/22620 A1 | | 6/1997 |

OTHER PUBLICATIONS

Moretto et al, Int. J. Peptide Protein Res. ,1992, vol. 40, pp282–293.*
Spencer et al, J. Org. Chemistry, 1993, vol. 58, pp1635–1638.*
Toniolo et al, Biopolymers, 1993, vol. 33 pp 1061–1072.*

Amsberry et al., "Amine prodrugs which utilize Hydroxy Amide Lactonization. A Potential Esterase–Sensitive Amide Prodrug," *Pharmaceutical Research*, (New York, NY, U.S.), 8:4:455–461, XP000607607, ISSN:0724–8741, cited in the application, the whole document (Apr. 4, 1999).
Creighton et al., "Mechanistic studies of an unusual amide bond scission," *Journal of the American Chemical Society*, (D.C., U.S.), 121:29:6786–6791, XP002155724, the whole document, (Jul. 14, 1999).
Jones et al., "Peptides. XIX. Isomerization of oxazolones derived from tripeptides," *Chemical Abstracts*, (Columbus, Ohio, U.S.), abstract No. 5205d, p. 5205, col. 1, XP002155729, abstract, (Feb. 14, 1966) & Tetrahedron, (Oxford, GB), 21:11, pp. 3209–3218 (1965).
Moretto et al., "Monomer units for the beta–bend ribbon structure: MeAib peptides," *Chemical Abstracts*, (Columbus, Ohio, U.S.) 117:21, abstract No. 212940r, p. 896, col. 1, XP002155899, abstract, & *Int. J. Biol. Macromol.*, 14:4, pp. 178–184 (1992).
Paterson et al., "Sensitivity of polypeptide conformation to geometry. Theoretical conformational analysis of oligomers of alpha–aminoisobutyric acid," *Journal of American Chemical Society*, (D.C., U.S.), 103:11:2947–2955, XP002155727, the whole document, (1981).

(List continued on next page.)

*Primary Examiner*—Paul J. Killos
*Assistant Examiner*—Héctor M Reyes
(74) *Attorney, Agent, or Firm*—Gary, Cary, Ware & Friedrich LLP; Lisa A. Haile (57) ABSTRACT

This invention relates to chemical compositions useful in protecting amino functional groups, e.g., during synthetic organic chemistry procedures or in the formulation and/or delivery of prodrugs. The present invention relates particularly to amino-protecting species comprising an acyl group that can form an amide bond with an amino group. The protecting groups of the present invention can be conveniently removed under a wide variety of conditions.

12 Claims, 2 Drawing Sheets

OTHER PUBLICATIONS

Spencer et al., "Comparative study of methods to couple hindered peptides," *International Journal of Peptide and Protein Research* (DK, Munksgaard, Copenhagen), 40:3/4:282–293, XP000311238, ISSN: 0367–8377, p. 289, (Sep. 1, 1992).

Spencer et al., "Unusual peptide bond cleavage reactions during acidolytic deprotection reactions," *Journal of Organic Chemistry*, (Easton, U.S.), 58:6:1635–1638, XP002155725, the whole document, (1993).

Toniolo et al., "Structures of peptides from &–amino acids methylated at the &–carbon," *Biopolymers*, (NewYork, NY, U.S.) 33:1061–1072, XP002155728, ISSN: 0006–3525, p. 1061–1063, table 1, (1993).

Zhu and Hegedus, "Incorporation of chromium aminocarbene complex–derived," *Journal of Organic Chemistry*, (Easton, U.S.), 60:18:5831–5837, XP002155726, p. 5834, col. 2, paragraph 2; p. 5835, col. 2, last paragraph to p. 5836, col. 1, first paragraph, (1995).

Brady, J.E., Humiston, G.E. General Chemistry, Principles and Structure, Third Edition, 1982.*

Spencer et al, Int. J. Peptide Protein Res. 1992, vol. 40, pp. 282–293.*

Spencer et al, J. Org. Chem. 1993, vol. 58 pp. 1635–1638.*

Toniolo, et al , Biopolymers, 1993, vol. 33 pp. 1061–1072.*

Amsberry and Borchardt, "The Lactonization of 2'–Hydroxyhydrocinnamic Acid Amides: A Potential Prodrug for Amines," *J. Org. Chem.*, 55:5867–5877 (1990).

Gangwar et al., "Synthesis of a Novel Esterase–Sensitive Cyclic Prodrug of a Hexapeptide Using an (Acyloxy)alkoxy Promoiety," *J. Org. Chem.*, 62:1356–1362 (1997).

Shan et al., "Prodrug Strategies Based on Intramolecular Cyclization Reactions," *Journal of Pharmaceutical Sciences*, 86(7):765–767 (1997).

* cited by examiner

N-SUBSTITUTED ALKYLAMINO ACIDS FOR USE AS AMINO-PROTECTING GROUPS

RELATED APPLICATIONS

This application claims the benefit of priority to U.S. provisional application Ser. No. 60/157,435, filed Oct. 4, 1999.

FIELD OF THE INVENTION

This invention relates to chemical species that are useful in protecting amino functional groups. The present invention relates particularly to amino-protecting species comprising a defined class of acyl compounds that can form an amide bond with an amino group.

BACKGROUND OF THE INVENTION

The amino functional group is found in many biologically important molecules such as amino acids, peptides, polypeptides, proteins, nucleosides, nucleotides, nucleic acids, glycosides, carbohydrate derivatives, alkaloids, and natural products. For most synthetic strategies amino groups must be protected. The utility of any protecting group depends on three considerations: (1) the ease of attaching the protecting group; (2) the ease of removing the protecting group; and (3) the compatibility of the protecting group with synthetic manipulations carried out on the molecule during the synthetic program.

Protection of an amino group is generally carried out by either acylation or alkylation. Both protection methods have advantages and disadvantages. Typically, alkylation is not the first choice for a protection strategy because overalkylation is difficult to control. Acylation of amino groups produces amides, which are easily formed under mild conditions. However, most amides are difficult to hydrolyze. Typically, unmasking an amino group from an amide is accomplished using harsh reaction conditions, e.g. boiling 6N HCl, which is incompatible with most complex synthetic programs. The trifluoroalkylamide is an exception since it can be removed by relatively mild alkaline conditions. Problems associated with the amide-based amino protection strategy may be circumvented using a carbamate protecting group (a special class of acylation-based amino protection). Examples of carbamates utilized in synthetic programs are benzyloxycarbonyl (Cbz), t-butyloxycarbonyl (Boc) and 9-fluoronylmethyl (Fmoc) carbamates. Carbamates are considered state of the art in protection of the amino functional group. However, appropriate amide-based amino protecting groups which can be easily removed under a variety of reaction conditions are still needed in modern synthetic organic chemistry.

Protecting groups may also be used in biological applications for use as prodrugs. The prodrug approach is viewed as one strategy for efficient delivery of lead compounds to the therapeutic site. The design of prodrugs is disclosed, for example, by Shan, D., et al. 1997 J Pharm Sci 765–767; Gangwar, S. et al. 1997 J Org Chem 1356–1362; and Amsberry, K., et al. 1990 J Org Chem 5867–5877, which are incorporated herein by reference. This approach has been particularly effective when prodrugs involve the conversion of a carboxylic acid to an ester, which can be readily hydrolyzed in vivo to release the parent drug. Application of the approach becomes problematic when applied to drugs containing amino groups. First, the chemical and enzymatic stabilities of amide bonds are much higher than those of ester bonds. Secondly, regeneration of an amine drug from the amide prodrug is difficult. The prodrugs of the present invention address both of these problems.

SUMMARY OF THE INVENTION

In accordance with the invention, there are provided acylated amino protecting groups that can be cleaved under a prescribed set of acidic conditions ranging from highly acidic to very mildly acidic. Substituents on the acyl moiety of the invention protecting group can be widely varied to facilitate removal of the protecting group under a wide range of acidic reaction conditions. Accordingly, this family of amino-protecting groups can be used in conjunction with a variety of applications ranging from complex chemical syntheses to biological applications such as drug delivery.

In accordance with another aspect of the invention, there are provided prodrug compositions useful for improving the bioavailability of pharmaceutically active agents.

In accordance with yet another aspect of the invention, there are provided methods for improving the bioavailability of pharmaceutically active agents.

In accordance with still another aspect of the invention, there are provided pre-prodrug compositions useful for delivering acid-activated prodrugs to acidic environments in vivo.

In accordance with a further aspect of the invention, there are provided methods for delivering acid-activated prodrugs to acidic environments in vivo.

In accordance with a still further aspect of the invention, there are provided methods for protecting an amino group during a chemical synthesis.

DETAILED DESCRIPTION OF THE INVENTION

In accordance with the present invention, there are provided protected amino-substituted compounds bearing acylated amino protecting groups having the following structure:

wherein
X is —H, alkyl, substituted alkyl, alkenyl, substituted alkenyl, alkynyl, substituted alkynyl, aryl, substituted aryl, heterocyclic, substituted heterocyclic, alkoxy, substituted alkoxy, alkenoxy, substituted alkenoxy, and the like, and R is any amino-bearing molecule, including biologically active molecules such as amino acids (naturally occurring or non-naturally occurring), peptides, polypeptides, nucleosides, nucleotides, nucleic acids, glycosides, carbohydrate derivatives, alkaloids, natural products, hormones, proteins, and the like.

As used herein, the term "alkyl" refers to a monovalent straight or branched chain radical of from 1 to about 24 carbon atoms, including, but not limited to, methyl, ethyl, n-propyl, isopropyl, n-butyl, isobutyl, tert-butyl, n-hexyl, and the like.

As used herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As used herein, "alkenyl" refers to straight or branched chain hydrocarbyl groups having one or more carbon-carbon double bonds, and having in the range of about 2 up to 24 carbon atoms (e.g., ethenyl, propenyl, butenyl, pentenyl, etc.), and "substituted alkenyl" refers to alkenyl groups further bearing one or more substituents as set forth above.

As used herein, "alkynyl" refers to straight or branched chain hydrocarbyl groups having one or more carbon-carbon triple bonds, and having in the range of about 2 up to 24 carbon atoms (e.g., propargyl, propynyl, butynyl, pentynyl, etc.), and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heterocyclic" refers to aromatic groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "alkoxy" refers to a straight or branched chain hydrocarbyl group of from 1 to about 24 carbon atoms which is attached to an oxygen atom and "substituted alkoxy" refers to alkoxy groups further bearing one or more substituents as set forth above.

As used herein, "alkenoxy" refers to a straight or branched chain hydrocarbyl group of about 2 up to 24 carbon atoms having one or more carbon-carbon double bonds which is attached to an oxygen atom and "substituted alkenoxy" refers to alkenoxy groups further bearing one or more substituents as set forth above.

The term "non-interfering organic radical" refers to any substituent present on the protecting group which is not deleterious to its efficacy as an amino-protecting group.

In one aspect of the invention, there is provided the ability to control an intramolecular cleavage reaction to remove the protecting group from the amino-bearing compound. This is demonstrated herein by removal of the acylated N-methyl-α-aminoisobutyryl (NMeAib) moiety by exposure of the compound to predetermined acidolysis conditions. The acid sensitivity of the protecting group can be adjusted by suitable modification of the acyl portion of the NMeAib residue. Thus, the present invention provides a wide range of acylated amino protecting groups removable under predetermined acidic conditions.

While not wishing to be bound by any particular theory, the mechanism of the intramolecular cleavage reaction is believed to be based upon the amide bond scission illustrated in Scheme 1.*

*The formula designations for the acyl N-methyl-α-aminoisobutyric acid resifues are interchangeably shown as follows, wherein the methyl groups are either explicitly stated or implicitly designated based on the conventional line-drawing techniques of organic chemistry:

In accordance with the present invention, it has been discovered that the rate of reaction can be altered simply by modifying X. Thus, for electron-donating X groups the rate of scission (the sensitivity to acidic conditions) increases. The opposite effect holds true for electron-withdrawing X groups. Table 1 illustrates the effect of X on the rate of deprotection of phenylalanine methyl ester. Four p-substituted benzoyl-N—MeAib—Phe—OMe (7a–d) compounds were subjected to acidic conditions (2% trifluoroacetic acid (TFA) in acetonitrile) and the rate of scission measured for each protecting group.

TABLE 1

Acidolysis of p-X—$C_6H_4C(O)$—NMeAib-Phe-OMe with 2% TFA in acetonitrile.

| Compound | k (s$^{-1}$) | Half-life (h) | σ |
|---|---|---|---|
| NO$_2$ | 1.5 × 10$^{-5}$ ± 0.1 × 10$^{-5}$ | 12 | 0.78 |
| CN | 2.3 × 10$^{-5}$ ± 0.1 × 10$^{-5}$ | 8 | 0.66 |
| CF$_3$ | 3.7 × 10$^{-5}$ ± 0.2 × 10$^{-5}$ | 5 | 0.54 |
| Cl | 8.3 × 10$^{-5}$ ± 0.3 × 10$^{-5}$ | 2 | 0.23 |
| H | 1.7 × 10$^{-4}$ | 1 | 0.00 |

The measured half-lives demonstrate the electronic effect of the para substituents on the stability of the scissile bond. The half-life for the extremely electron-withdrawing NO$_2$ substituent was determined to be about 12 hours and the modestly electron-withdrawing Cl exhibited a half-life of about 2 hours. The Hammett series (Table 1) exhibits a linear free energy relationship with the normalized dissociation constants (σ) of their parent benzoic acids (FIG. 1).

Figure 1:
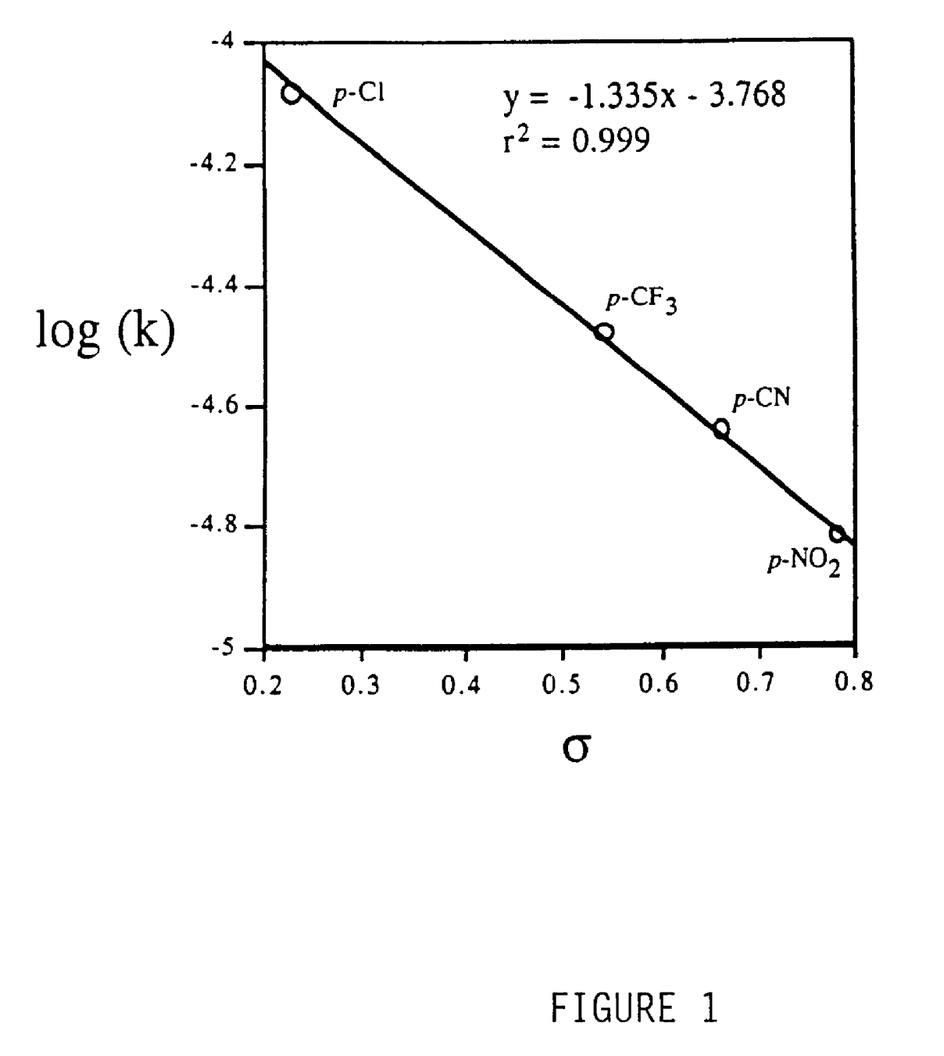
FIG. 1 depicts a Linear Free Energy Diagram wherein the log $10_k$ is plotted versus σ for the cleavage of p-X—$C_6H_4C$(O)—NMe—Aib—Phe—OMe in 2% TFA in $CH_3CN$, wherein X represents the functional groups Cl, $CF_3$, CN, $NO_2$.

The equation representing the line in FIG. 1 is particularly useful because it allows one to predict the rate of scission for any m-substituted or p-substituted X—$C_6H_4C(O)$—NMeAib amide where a for the parent acid is known. For example, when X is a strong electron donor such as dimethylamino, the half life for the protected amine p-N$(CH_3)_2C_6H_4C(O)$—NMeAib is substantially less than with the electron-withdrawing substituent discussed above, e.g., about 29 seconds; Therefore, by is carefully selecting the X substituent, one can exert substantial control over the sensitivity of the scissile bond to pH conditions (Hansch, C., et al. *Aromatic Substituent Constants for Structure-Activity Correlations* J Med Chem 16(11):1207–1213 (1973), which is incorporated by reference herein in its entirety).

The NMeAib species is the presently preferred NAlkylAib species. While not intending to be bound by theory, it is presently believed that the NMeAib group is more effective for the reaction because the N-methyl group and the methyl group α to the amide linkage are eclipsing, pushing the carbonyls into a gauche configuration, which is the lowest energy configuration for the molecule, Scheme 2a.

Scheme 2a

If, however, one methyl group α to the amide linkage is removed, the gauche carbonyl energy state becomes much higher than any other energy state, Scheme 2b.

Scheme 2b

This is reflected in the reaction rate for the cleavage of acylated NMeAla—Amino Acid—OMe where $t_{1/2}$ is measured in days as compared to acylated NMeAib—Phe—OMe where $t_{1/2}$ is approximately 22 minutes. The mechanism and energetics of deprotection/cleavage of these groups is diclosed in Urban, J., et al. *Lability of N-alkylated peptides towards TEA cleavage.* Int. J Peptide Protein Res 47:182–189 (1997), which is incorporated by reference its entirety.

The utility of the acylated amino protecting methodology of the invention was demonstrated by synthesizing the tetrapeptide H—Phe—Leu—Val—Phe—OH (SEQ ID NO: 1) on solid support. Synthesis of the protected amino acid building blocks employed for the synthesis of SEQ ID NO: 1 is described in Example 4 and illustrated in Scheme 3.

EDC = 1-(3-dimethylaminopropyl)-3-ethylcarbodiimide hydrochloride
HOBt = 1-hydroxybenzotriazole

These protected amino acid building blocks were then employed to synthesize SEQ ID NO: 1, compound 22, as illustrated in Scheme 4, wherein the solid circles represent the solid support.

DIEA = diisopropylethylamine
DIC = diisopropylcarbodiimide

It should be understood that the invention is not limited to amino acid protection. Examples of amino group protection encompass but are not limited to such molecules as peptides, polypeptides, proteins, nucleosides, nucleotides, nucleic acids, natural products, hormones, glycosides, biogenic amines, alkaloids, and the like. For example, a protected species according to the invention can be the histamine adduct shown below:

or the serotonin adduct shown below:

Additionally, Scheme 5 illustrates the application of the invention wherein an orthogonally protected ornithine is incorporated into the synthesis of a fibrinogen peptide H—Gly—Pro—Arg—Pro—OH, 33, (SEQ ID NO: 2).

Scheme 5

Synthesis of compound 33 is initiated by coupling H—Pro—OBn 23 with compound 24 using EDC/HOBt to form dipeptide 25. It should be noted that compound 25 has two benzoyl-NMeAib-protected amines. The α amino protecting group can be selectively removed while leaving the δ amino-protecting group intact simply by taking advantage of their differing sensitivities to acid removal conditions. By exposing 25 to mild acidic conditions (2% TFA in acetonitrile) the p-methoxy-benzoyl-NMeAib ($t_{1/2}$=20 min) is removed while leaving the p-nitro-benzoyl-NMeAib ($t_{1/2}$=12h) intact yielding compound 26. The p-methoxy-benzoyl-NMeAib—Pro—OH 27 is allowed to react with compound 26 using EDC/HOBt to yield compound 28. Acidolysis of the p-methoxy benzoyl NMeAib liberates the secondary amine of proline to produce tripeptide 29 which is coupled to Cbz—Gly—OH yielding compound 30. Removal of the p-nitro-benzoyl-NMeAib amino-protecting group prepares the δ amine of 31 for guanidinylation with the reagent N,N'-bis-CBz-triflyl guanidine. Subsequent hydrogenolysis of the benzyl ester and benzyloxycarbonyl protecting groups of compound 32 produces the final product H—Gly—Pro—Arg—Pro—OH 33, SEQ ID NO: 2.

Figure 2:
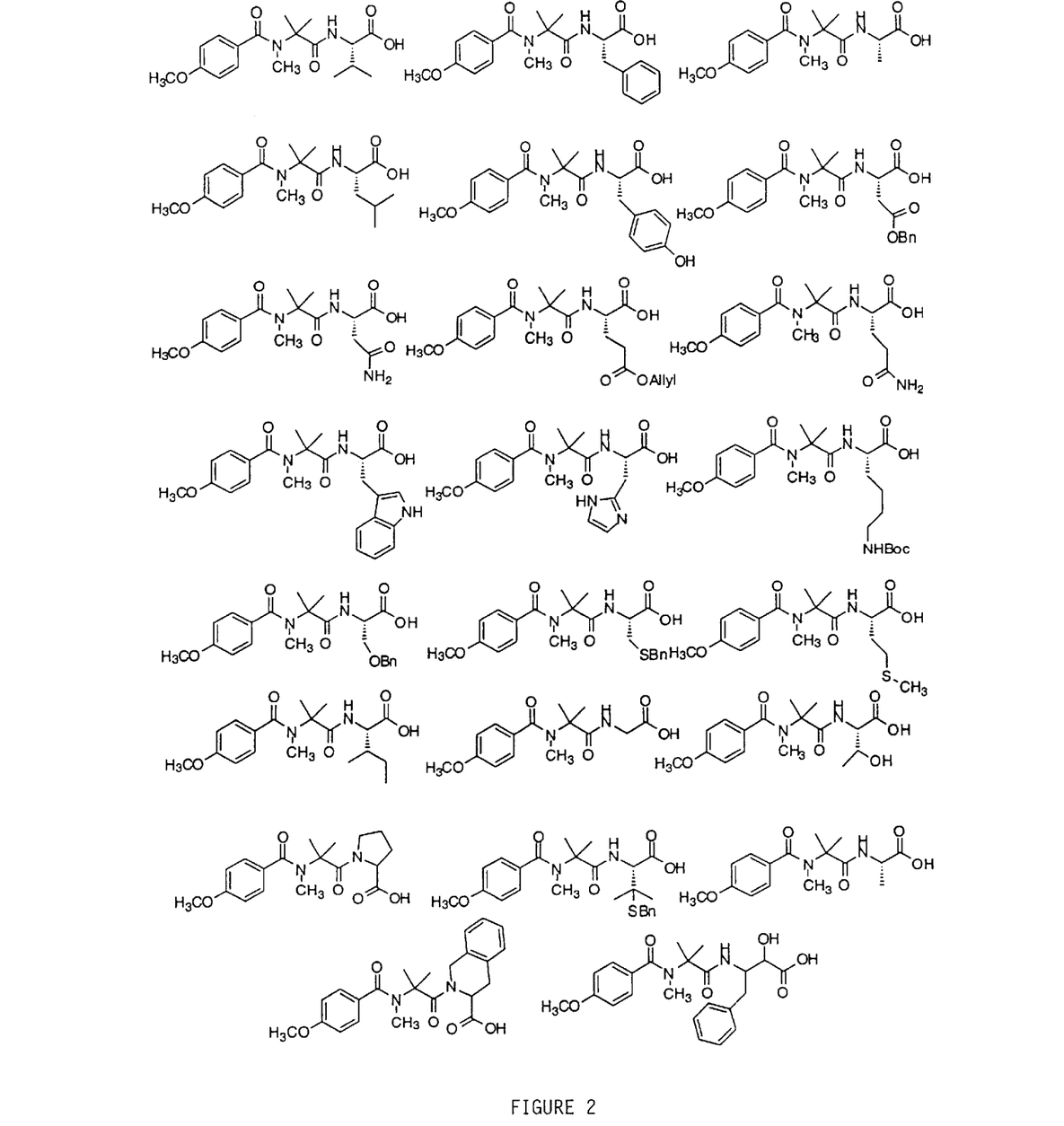
FIG. 2 depicts examples of representative natural and unnatural amino acids protected by the N-p-methoxybenzoyl-N-methyl-α-aminoisobutyryl group.

Acylated N-methyl-α-aminoisobutyryl amides of all of the natural amino acids are also within the scope of the invention. FIG. 2 contains structures for a number of p-methoxy-benzoyl-NMeAib-amino acids useful in accordance with the present invention for peptide synthesis. The invention also includes similarly protected unnatural amino acids and amines.

Another aspect of the present invention provides prodrugs of pharmaceutically active agents for improved in vivo delivery. The optimization of the in vivo activity of any drug depends on two factors. The potency of the ligand at the target site is as important as its efficient delivery thereto. The discovery of a lead compound can now be accomplished relatively quickly with powerful approaches such as rational design, chemical diversity, and high throughput screening. Efficient delivery of the lead compound remains a challenge. Drug candidates must have physiochemical properties that allow permeation of biological barriers, for example, the blood-brain barrier (BBB) to the central nervous system (CNS) or the intestinal mucosal barrier (IMB) to the lymphatic transport system. The modifications required for improved delivery of a molecule must not compromise its intrinsic biological potency.

The prodrugs of the present invention have the following structure:

wherein
X is H, alkyl, substituted alkyl, alkenyl, substituted alkenyl, alkynyl, substituted alkynyl, aryl, substituted aryl, heterocyclic, substituted heterocyclic, alkoxy, substituted alkoxy, alkenoxy, substituted alkenoxy, and the like, and
D is an amino-bearing pharmaceutically active agent.

The amino protecting groups of the invention, acylated N-methyl-α-aminoisobutyryl groups, offer useful, programmable acid-labile masking agents to prepare amide-based prodrugs. According to one embodiment of this aspect of the invention, γ-amino butyric acid (GABA) which does not cross the blood brain barrier, is modified to become a prodrug of the invention. GABA acts on the CNS by reducing the levels of dopamine, in turn attenuating the cravings associated with abuse of cocaine, nicotine and methamphetamine.

Scheme 6 illustrates the release of GABA, 36, from the acylated N-methyl-α-amino-isobutyryl GABA prodrug, 34.

By modifying X, one is able to vary the sensitivity of the prodrug to acidic conditions. This technology can be applied to improve the oral bioavailability and biostability of peptides and peptidomimetics simply by incorporation of acylated N-methyl-α-aminoisobutyryl groups into peptides and peptidomimetics. A prodrug strategy utilizing the acylated N-methyl-α-aminoisobutyryl masking agent to form a pro- drug containing Leu[5]enkephalin is shown in Scheme 7.

It is known that Leu[5]enkephalin is highly active at the δ-opioid receptor, yet it exhibits poor bioavailability and biostability. Conversion of Leu[5]enkephalin into a prodrug according to the present invention takes advantage of the stability of cyclopeptides to enzymatic degradation and captures the advantages of a prodrug delivery approach, (e.g., higher concentration of active ingredient at the active site, minimization of deleterious side effects). The cleavage of c[NMeAib—Tyr—Gly—Gly—Phe] (SEQ ID NO: 3), 37, liberating the active linear enkephalin analog H—Tyr—Gly—Gly—Phe—NMeAib—OH, (SEQ ID NO: 4), 38, is achieved under acidic conditions. The cyclopentapeptide is reasonably stable to the enzymatic degradation process while the increased hydrophobic property adapts the molecule to cross the BBB to the target therapeutic site. In preferred embodiments of the invention, other opioids and pharmaceutically active compounds that exhibit poor bioavailability and biostability such as aminoglycosides, RGD peptides, somatostatins, and the like, can similarly be converted to amino-protected prodrugs.

In accordance with another aspect of the invention there are provided pre-prodrug compositions of pharmaceutically active agents. This aspect of the invention contemplates the conversion of drugs containing amino groups into acylated NMeAib amino-protected species, thereby enhancing the ability of the drug to permeate biological barriers for delivery to a target site.

The pre-prodrug compositions of the invention have the following structure:

wherein
R is H, alkyl, substituted alkyl, alkenyl, substituted alkenyl, alkynyl, substituted alkynyl, aryl, substituted aryl, heterocyclic, substituted heterocyclic, alkoxy, substituted alkoxy, alkenoxy, substituted alkenoxy, and the like, and X is alkylene, substituted alkylene, alkenylene, substituted alkenylene, alkynylene, substituted alkynylene, arylene, substituted arylene, heterocyclic, substituted heterocyclic, alkoxylene, substituted alkoxylene, alkenoxylene, substituted alkenoxylene, and the like, and D is an amino-substituted pharmaceutically active agent.

In order to release the drug for its intended use, the prodrug must be exposed to an acidic environment. An example of the use of a pre-prodrug according to the present invention is illustrated in Scheme 8.

Scheme 8

Pre-ProDrug
39

ProDrug
40

Delivery agent
41

Drug
42

The pre-proderivative of GABA (39) is administered and because of its hydrophobic character is absorbed into the CNS via the bloodstream. Once in the CNS the pre-prodrug is exposed to an esterase, liberating the carboxylic acid to produce the prodrug, 40. The carboxylic acid is in close proximity to the carbonyl oxygen of the scissile bond. Activation of the labile bond via protonation of the scissile carbonyl oxygen initiates the cleavage reaction and releases the drug 42 from the prodrug. As readily recognized by those of skill in the art, based on the present disclosure, it is possible to modify the R group of the ester or the X group of the acylated N-methyl-(α-aminoisobutyric amide of the pre-prodrug, thus allowing the rate-determining step to be varied for the release of the drug (either ester hydrolysis or amide acidolysis).

In accordance with a further aspect of the invention, there are provided pharmaceutical formulations comprising amino-protected drugs according to the present invention. These formulations can be administered either parenterally, orally or topically in a manner similar to formulations comprising a non-protected drug. The therapeutically effective amount of the amino-protected drug to be used is determined with reference to the recommended doses of the non-protected drug, bearing in mind that in selecting the appropriate dosage in any specific case, consideration must be given to the patent's weight, general health, metabolism, age, and other factors that influence response to the drug. The dosage for a mammal, including a human, therefore may vary depending on the drug and the subject to be treated. Conventionally, the parenteral dose is from 20% to 100% of the appropriate orally administered dose.

The invention will now be described in greater detail by reference to the following non-limiting examples.

EXAMPLES

General Considerations

The chemical reactions described below are disclosed in terms of their general application to the preparation of the protected amino-containing species of the invention. Occasionally, the reaction may not be applicable as described to every species within the claimed scope of the invention. The species for which this occurs will be readily recognized by those skilled in the art. In all such cases, the reaction can be successfully performed by conventional modifications known to those skilled in the art, e.g., by appropriate protection of interfering groups, by changing to alternative conventional reagents, or by routine modification of reaction conditions. Alternatively, other reactions disclosed herein or otherwise conventional will be applicable to the corresponding protected amino groups according to the invention. In all preparative methods, all starting materials are known or readily prepared from known starting reagents.

All temperatures are in degrees Celsius (° C.)

All amino acids were of L configuration and were obtained from Bachem Bioscience, Inc., King of Prussia, Penn. 19406. ACS-grade and HPLC-grade solvents were purchased from Fisher Scientific and used without further purification. TEA was purchased from Aldrich Chemical. HOBt, TFA (HPLC grade) and HCl/dioxane (4N) were purchased from Chem-Impex International.

Mass positive (FAB) spectra were obtained using m-nitrobenzyl alcohol as a matrix. Column chromatography was performed using silica gel 60 from Merck. All reagents and solvents were used as received from the vendors. Thin layer chromatography for each compound is reported in $R_f$ where the mobile phase was 90:10:1 chloroform, methanol, acetic acid v:v. Compounds not subjected to elemental analysis were analyzed using RP-HPLC and FAB-HRMS. Analytical RP-HPLC was carried out on a Waters 510 dual pump system using a Vydac C18 (218TP54) column and a Waters 996 photodiode array detector. The gradient mobile phase started at 15/85 (0.1% TFA) acetonitrile/water and ended at 85/15 acetonitrile/water over 30 minutes.

$^1$H NMR spectra were obtained on a home built spectrometer using a 360 MHz Oxford Instruments magnet with a Tecmag pulse digitzer/programmer. All spectra were recorded at ambient temperature. The $^1$H NMR chemical shifts are expressed relative to $CHCl_3$ (7.24 ppm) or DMSO (2.49 ppm).

Example 1

Synthesis of the Ac—NMeAib derivative of phenylalanine methyl ester, Ac—NMeAib—Phe—OMe A. Boc—NMeAib—OH. To a solution of Boc—NMeAib—OMe (35.3 g, 153 mmol) in MeOH (450 mL)

was added a solution of 85% KOH (50 g, 750 mmol) in water (225 mL). The resulting solution was stirred and heated to 60–65° C. for 24 h. The solution was concentrated in vacuo to remove most of the MeOH. The residual aqueous solution was acidified to pH<2 with conc. HCl, then extracted with EtOAc (400 mL). The organic layer was washed with brine (200 mL) and dried over $Na_2SO_4$. The solution was concentrated in vacuo until crystallization of the product began. The mixture was diluted with hexane and the insoluble material collected by filtration, washed with hexane, and dried to give the product: 20.1 g of a fluffy white crystalline solid (60%). mp 153° C. $^1$H NMR (DMSO-$d_6$ δ) 1.32 & 1.35 (2 s, 15H, Boc & β-$CH_3$), 2.79 (s, 3H, N—$CH_3$), 12.08 (s, 1H, COOH). $R_f$=0.53. HRMS-FAB (m/z) [M+Na]$^+$ calculated for $C_{10}H_{19}NO_4$, 240.1212 found 240.1214.

B. Boc—NMeAib—Phe—OMe. To a solution of Boc—NMeAib—OH (10.0 g, 46.04 mmol), H—Phe—OMe, HCl salt (11.92 g, 55.25 mmol), 1-hydroxybenzotriazole (HOBt) (5.30 g, 46.04 mmol), triethylamine (TEA) (8.0 mL, 55.25 mmol) in 150 mL $CH_2Cl_2$ (150 mL) was added dicyclohexylcarbodiimide (DCC) (9.50 g, 46.04 mmol). The resulting solution was stirred at room temperature for 24 hours and filtered. The solvent was removed in vacuo and the residue partitioned between EtOAc (250 mL) and 1M HCl (50 mL). The organic layer was washed with 1M HCl (2×50 mL), brine (25 mL) and 10% aq. $Na_2CO_3$ (3×50 mL), brine (25 mL) and dried over $Na_2SO_4$. The solvent was removed in vacuo to give the product: 13 g yellow oil (75%). $^1$H NMR (CDCl$_3$ δ)1.4 & 1.42 (2 s, 15H, Boc & β-$CH_3$), 2.80 (s, 3H, N—$CH_3$ ), 3.10 (m, 2H, β-$CH_2$ Phe), 3.6 (s, 3H O—$CH_3$), 4.83 (dd, 1H, J=13.3 Hz, J=5.8 Hz, α-CH Phe), 6.3 (d, 1H, J=5.6 Hz, NH), 7.2 (m, 5H, $C_6H_5$ Phe).

C. H—NMeAib—Phe—OMe, HCl salt. A solution of Boc—NMeAib—Phe—OMe (13 g 34.4 mmol) in a mixture of anhydrous HCl in dioxane (4N, 50 mL) was stirred at room temperature and rapidly evolved gas. After 30 min, the solvent was removed in vacuo and the residual solid triturated with ethyl ether. The solid which formed was collected by filtration, washed with ethyl ether, and dried under vacuum to give the product: 10.4 g of a white solid (97%). $^1$H NMR (DMSO-$d_6$ δ) 1.3 (s, 15H, Boc), 1.35 (s, 6H, β-$CH_3$ Aib), 2.1 (br, s, 3H, $NCH_3$), 3.0 (m, 1H, β-$CH_2$ Phe), 3.2 (m, 1H, δ-$CH_2$ Phe), 3.7 (s, 3H, O—$CH_3$), 4.53 (m, 1H, α-CH Phe), 7.2 (m, 5H, $C_6H_5$ Phe); 9.2 ( d, J=5.0 Hz, NH Phe), 9.2 (Br s, $NH_2CH_3$). HRMS-FAB (m/z) [M+H]$^+$ calculated for $Cl_5H_{22}N_2O_3$.

D. Acetyl-NMeAib—Phe—OMe. To a round bottom NMeAib—Phe—OMe, HCl salt (0.300 g, 0.95 mmol) and TEA (0.3 mL, 2.0 mmol) was dissolved in $CH_2Cl_2$. Acetyl chloride (0.068 mL 0.95 mmol) was added and the solution was stirred for 24 hours. The solvent was removed in vacuo and the residue was dissolved in EtOAc (50 mL) and washed with 1M HCl (3×10 mL), brine (1×5 mL), 10% $Na_2CO_3$ (3×10 mL), brine (1×5 mL) and dried with anhydrous $Na_2SO_4$. The ethyl acetate was removed in vacuo and the resulting oil was chromatographed with silica gel (50/50 hexanes ethyl acetate) to give a clear oil. This oil was crystallized upon trituration with ethyl ether 0.124 g isolated (45%). $^1$H NMR (CDCl$_3$ δ) 1.38 (s, 6H, β-$CH_3$ Aib); 2.05 (s, 3H, Ac), 2.93 (s, 3H, N—$CH_3$), 3.11 (m, 2H, β-$CH_3$ Phe), 3.7 (s, 3H, O—$CH_3$), 4.9 (q, 1H, α-CH Phe, J=7.2 Hz), 6.08 (d, 1H, J=7.2 Hz, NH), 7.2 (m, 5H, $C_6H_5$). HRMS-FAB (m/z) [M+Na]$^+$ calculated for $Cl_{17}H_{24}N_2O_4$.

Example 2

Synthesis of the Pr—NMeAib Derivative of phenylalanine,Pr—NMeAib—Phe—OMe

Steps A–C as described in Example 1 are repeated, as is step D, employing propionic acid (instead of acetyl chloride as the acylating agent). Thus, propionic acid (0.237 mL 3.17 mmol) 1-hydroxy-7-azabenzotriazole (HOAt) (0.43 g, 3.17 mmol) and DCC (0.66 g, 3.17 mmol) were added to a round bottom flask and allowed to react to form the Pr-OAt for 20 min. The dicyclohexylurea (DCU) was filtered off through a tared glass frit fimnel and washed with $CH_2Cl_2$ (2×1 mL). To the Pr-OAt solution, NMeAib—Phe—OMe, HCl salt (1.0 g, 3.17 mmol) and TEA (1.0 mL, 6.3 mmol) were added and a yellow color was observed. This solution was allowed to react overnight. The solvent was removed in vacuo and the residue was dissolved in EtOAc (50 mL) and washed with 1M HCl (3×10 mL), brine (1×5 mL), 10% $Na_2CO_3$ (3×10 mL), brine (1×5 mL) and dried with anhydrous $Na_2SO_4$. The ethyl acetate was removed in vacuo and the resulting oil was chromatographed with silica gel (50/50 hexanes ethyl acetate) to give a clear oil. This oil was crystallized upon trituration with ethyl ether (52%). $^1$H NMR (CDCl$_3$ δ) 7.21 (m, 5H, Phe), 6.15 (d, 1H, J=7.2 Hz, NH), 4.85 (dd, 1H, J=5.8, J=13.0, αCH), 3.66 (s, 3H, $OCH_3$), 3.10 (m, 2H, β-$CH_2$), 2.91 (s, 3H, N—$CH_3$), 2.30 (m, 2H, CH2, Pr), 1.38 (s, 3H, Aib), 1.37 (s, 3H, Aib), 1.06 (t, 3H, J=7.6, $CH_3$ Pr).

Example 3

General Procedure for the Synthesis of p-X—BnC (O)—NMeAib—OMe

The following procedure describes in detail the synthesis of a variety of p-substituted benzoyl amino-protecting groups for the protection of phenylalanine.

p-$NO_2$—$C_6H_4$—C(O)—NMeAib—Phe—OMe (7a). To a stirred solution of H—NMeAib—Phe—OMe, HCl salt (0.3 g, 1.0 mmol) in $CH_2Cl_2$ (3mL) was added TEA (0.28 mL, 2.0 mmol). After stirring for 5 min at room temperature p-nitrobenzoyl chloride (0.15 g, 1 mmol) was added. The resulting solution was stirred at room temperature for 24 h. The solvent was removed in vacuo and redissolved in ethyl acetate (30 mL). The ethyl acetate layer was washed with 1M HCl (3×10 mL) brine (10 mL), 10% aq. $Na_2CO_3$ (3×10 mL), brine (10 mL), and dried over $Na_2SO_4$. Evaporation of the solvent was followed by column chromatography of the product with $CHCl_3$—MeOH-Acetic Acid (90:10:0.1 v:v:v) provided 7a (see Table 1) (100 mg 24%) as a pale yellow amorphous solid: mp.65–70° C.; $^1$H NMR (360 MHz CDCl$_3$ δ) 1.54 &1.52 (2s, 6H, β-MeAib), 2.87 (s, 3H, N—$CH_3$), 3.15 (d, 2H, J=5.04 Hz, β-H), 3.69 (s, 3H, O—$CH_3$), 4.86 (m, 1H, α-H); 6.35 (d, 1H, J=6.35 Hz, N—H), 7.20 (m, 5H, Aromatic Phe), 7.55 (d, 2H, J=8.64 Hz, Benzyl-H), 8.64 (d, 2H, J=8.64 Hz, Benzyl-H), FAB-MS m/z (relative intensity) 428 (35%), 450 (40%), 249 (100%); $[α]_D^{20}$–16.15° (c 0.014, MeOH).

p-CN—$C_6H_4$C(O)—NMeAib—Phe—OMe (7b). The same procedure as described above for the preparation of compound 7a was followed to provide 7b (see Table 1) (100 mg, 25%): mp.82–85° C.; $^1$H NMR (360 MHz CDCl$_3$ δ) 1.53 &1.54 (2s, 6H, δ-MeAib), 2.85 (s, 3H, N—$CH_3$), 3.15 (d, 2H, J=5.04 Hz, β-H), 3.69 (s, 3H, O—$CH_3$), 4.85 (m, 1H, α-H), 5.37 (d, 1H, J=6.0 Hz, N—H), 7.22 (m, 5H, Aromatic Phe), 7.49 (d, 2H, J=8.28 Hz, benzyl-H), 7.67 (d, 2H, J=8.28 Hz, Benzyl-H). $[α]_D^{20}$–21.1° (c0.009, MeOH). Anal. Calculated for $C_{23}H_{25}N_3O_4$: C, 67.80; H, 6.18; N, 10.31. Found C, 67.15; H, 6.26; N, 10.31.

p-$CF_3$—$C_6H_4$C(O)—NMeAib—Phe—OMe (7c). The same procedure as described above for the preparation of compound 7a was followed to provide 7c (see Table 1) (125 mg, 26%): mp.101–103° C.; $^1$H NMR (360 MHz CDCl$_3$ δ) 1.52 &1.54 (2s, 6H, β-MeAib), 2.86 (s, 3H, N—$CH_3$), 3.15

(d, 2H, J=5.4 Hz, β-H), 3.68 (s, 3H, O—CH$_3$), 4.86 (m, 1H, α-H); 6.37 (d, 1H, J=2.16 Hz, N—H), 7.18 (m, 5H, Aromatic Phe), 7.50 (d, 2H, J=7.56 Hz, Benzyl-H), 7.64 (d, 2H, J=7.56 Hz, Benzyl-H). [α]$_D^{20}$-2.30° (c 0.014, MeOH). Anal. Calculated for C$_{23}$H$_{25}$F$_3$N$_2$O$_4$: C, 61.33; H, 559; F, 12.65; N, 6.22. Found C, 61.32; H, 5.53; F, 12.67; N, 6.30.

p-Cl—C$_6$H$_4$C(O)—NMeAib—Phe—OMe (7d). The same procedure as described above for the preparation of compound 7a was followed to provide 7d (see Table 1) (100 mg 24%): mp.129–133° C.; $^1$H NMR (360 MHz CDCl$_3$ δ) 1.52 &1.53 (2s, 6H, β-MeAib), 2.90 (s, 3H, N—CH$_3$), 3.16 (d, 2H, J=5.4 Hz, β-H), 3.63 (s, 3H, O—CH$_3$), 4.86 (m, 1H, α-H), 6.40 (d, 1H, J=6.10 Hz, N—H), 7.15 (m, 5H, Aromatic Phe), 7.25 (d, 2H, J=7.56 Hz, Benzyl-H), 7.35 (d, 2H, J=7.56 Hz, Benzyl-H). MS C$_{22}$H$_{25}$ClN$_2$O$_4$ (MH$^+$) 417, (MNa$^+$) 439, (—Phe—OMe) 238; [α]$_D^{20}$-3.42° (c 0.013 MeOH). Anal. Calculated for C$_{22}$H$_{25}$ClN$_2$O$_4$: C, 63.38; H, 6.04; Cl, 8.50; N, 6.72. Found C, 63.01; H, 6.03; Cl, 8.46; N, 6.72.

Example 4

Synthesis of H—Phe—Leu—Val—Phe—OH (SEQ ID NO: 1) Using N-substituted alkylamino acid Protecting Groups Synthesis of protected amino acid building blocks employed for the synthesis of H—Phe—Leu—Val—Phe—OH (SEQ ID NO: 1) was carried out as illustrated in Scheme 3. Boc-protected 2-amino-isobutyric acid 10 (Boc—Aib—OH) was alkylated with methyl iodide to produce Boc—MeAib—OMe 11. The methyl ester was saponified with lithium hydroxide to form Boc—NMeAib—OH 12. Compound 12 was allowed to react with H—Val—OMe to form the dipeptide Boc-13. Removal of the Boc protecting group with trifluoroacetic acid (TFA) produced H—NMeAib—Val-OMe 14.

Acylation of H—NMeAib—Val—OMe with benzoyl chloride generated benzoyl-NMeAib—Val—OMe 15. Saponification of 15 with lithium hydroxide yielded the protected amino acid building block 16 ready for peptide synthesis. The same reaction sequence was used to prepare the other required building blocks, namely benzoyl-NMeAib—Leu—OH and benzoyl-NMeAib—Phe—OH.

These protected amino acid building blocks were subsequently used to synthesize H—Phe—Leu—Val—Phe—OH 22 (SEQ ID NO: 1) (Scheme 4). Synthesis of is peptide 22 on solid support was initiated allowing benzoyl NMeAib—Val—OMe 16 to react with H—Phe-Wang resin 17 using DIC, HOBt and DIEA to yield benzoyl-NMeAib—Val—Phe-Wang resin 18. The Kaiser ninhydrin test was negative, indicating complete coupling of the benzoyl-NMeAib—Val—OMe 16 to the resin bound phenylalanine. Acidolysis of the benzoyl-NMeAib protecting group was accomplished using TFA (7.5% in acetonitrile) yielding H—Val—Phe-Wang resin 19. Coupling of the Leu and Phe residues was achieved utilizing this peptide synthesis cycle. Removal of the peptide 22 from the Wang resin was accomplished using 100% TFA yielding the crude peptide. Analysis of H—Phe—Leu—Val—Phe—OH 22 (SEQ ID NO: 1) by analytical RP-HPLC indicated a 65% overall yield.

While the invention has been described in detail with reference to certain preferred embodiments thereof, it will be understood that modifications and variations are within the spirit and scope of that which is described and claimed.

What is claimed is:

1. A protected amino-substituted compound having the structure:

wherein

X is H, alkyl, alkenyl, substituted alkenyl, alkynyl, substituted alkynyl, aryl, substituted aryl, wherein the aryl group bears one substituent, heterocyclic, substituted heterocyclic, alkenoxy, or substituted alkenoxy, and R is a moiety bearing an amino group.

2. The protected amino-substituted compound according to claim 1 wherein X is alkyl.

3. The protected amino-substituted compound according to claim 2 wherein the alkyl is methyl or propyl.

4. The protected amino-substituted compound according to claim 1 wherein X is alkenyl.

5. The protected amino-substituted compound according to claim 4 wherein the alkenyl is ethenyl.

6. The protected amino-substituted compound according to claim 1 wherein X is alkynyl.

7. The protected amino-substituted compound according to claim 6 wherein the alkynyl is propargyl.

8. The protected amino-substituted compound according to claim 1 wherein X is substituted aryl wherein the aryl group bears one substituent.

9. The protected amino-substituted compound according to claim 8 wherein said substituted aryl contains a para-substituent.

10. The protected amino-substituted compound according to claim 8 wherein said substituent is alkoxy, nitro, cyano, haloalkyl or halogen.

11. The protected amino-substituted compound according to claim 10 wherein said substituent is alkoxy.

12. The protected amino-substituted compound according to claim 11 wherein said alkoxy is methoxy.

* * * * *